United States Patent [19]

Faithfull et al.

[11] Patent Number: 5,634,461
[45] Date of Patent: Jun. 3, 1997

[54] SYSTEM FOR MEASURING BLOOD OXYGEN LEVELS

[75] Inventors: Nicholas S. Faithfull, La Jolla; Glenn Rhoades, San Diego, both of Calif.

[73] Assignee: Alliance Pharmaceutical Corp., San Diego, Calif.

[21] Appl. No.: 487,086

[22] Filed: Jun. 7, 1995

[51] Int. Cl.[6] .................................................... A61B 5/00
[52] U.S. Cl. .......................... 128/637; 128/668; 128/672
[58] Field of Search ...................................... 128/632, 637, 128/668, 672, 687–689, 713

[56] References Cited

U.S. PATENT DOCUMENTS

| 4,562,843 | 1/1986 | Djorojovich et al. | 128/672 |
| 5,183,051 | 2/1993 | Kraidin et al. | |
| 5,217,019 | 6/1993 | Hughes | 128/713 |
| 5,398,680 | 3/1995 | Polson et al. | 128/687 |

FOREIGN PATENT DOCUMENTS

| 9423643 | 10/1994 | U.S.S.R. | 128/632 |

OTHER PUBLICATIONS

Fan, et al. "Effects of Hematocrit Variations on Regional Hemodynamics and Oxygen Transport in the Dog" Am. J. Physiol.: H545–H552 (1980).
Kelman, Richard. "Digital Computer Subroutine for the Conversion of Oxygen Tension into Saturation" J. Applied Physiol. 21(4):1375–1376 (1966).
Lundsgaard–Hansen, P. "Hemodilution–New Clothes for an Anemic Emperor" Vox Sang 36:321–336 (1979).
Lundsgaard–Hansen, et al. "Is There a Generally Valid, Minimum Acceptable Hemoglobin Level?" Infusionstherapie 16:167–175 (1989).
Mohsenifar, et al. "Relationship Between $O_2$ Delivery and $O_2$ Consumption in the Adult Respiratory Distress Syndrome" Chest 84(3):267–271 (1983).
Faithfull, et al. "A Program to Calculate Mixed Venous Oxygen Tension— A Guide to Transfusion"? *Oxygen Transport to Tissue XVI 361:* 41–49 eds. Hogan, et al. (1994).
Robertie, et al., "Safe Limits of Isovolemic Hemodilution and Recommendations for Erythrocyte Transfusion" Int'l Anesthesiology Clinics 28(4):197–204 (1990).
Severinghaus, J. "Blood Gas Calculator" J. Appl. Physiol. 21:1108–1116 (1966).
Shibutani, et al. "Critical Level of Oxygen Delivery in Anesthetized Man" Crit. Care Med. 11(8):640–643 (1983).
Hint, H. "The Pharmacology of Dextran and the Physiological Background for the Clinical Use of Rheomartodex and Macrodex" Acta Anaesthesiologica Belgica 2: 119–138 (1968).
Product Brochure from Waters Instruments, Inc., Rochester, MN 55903–6117 for MRM™ 6000 Metabolic Analyzer in 7 pgs.

*Primary Examiner*—Angela D. Sykes
*Assistant Examiner*—Stephen Huang
*Attorney, Agent, or Firm*—Knobbe, Martens, Olson & Bear

[57] ABSTRACT

A system and software is described for calculating, in real-time, the mixed venous partial pressure of oxygen in a patient. The system uses a computer, an arterial pressure line and a blood chemistry monitor to assist a physician with an on-line system for accurately determining when to give a patient a blood transfusion or otherwise alter the clinical management of that patient.

16 Claims, 3 Drawing Sheets

SYSTEM FOR MEASURING BLOOD OXYGEN LEVELS

FIELD OF THE INVENTION

This invention relates to systems and methods for determining levels of peripheral blood gases. Specifically, this invention relates to a system and method of determining, in real-time, the partial pressure of oxygen in a patient's mixed venous blood.

BACKGROUND OF THE INVENTION

One problem that has troubled physicians during the modern medical age is how to accurately measure the oxygenation state of a patient's tissues without resorting to an invasive procedure. This is important during many medical procedures because the physician needs to know when to transfuse more blood into a patient. When the oxygenation state of a patient's tissues is low, the physician should transfuse more blood or other oxygen carriers to increase the oxygen transportation rate. At the present time, most physicians rely on pulmonary artery catheterization to directly measure the oxygenation state of their patient's mixed venous blood during surgery. The physician then infers how well the patient's tissue is oxygenated from the measured oxygen content of the blood.

A physician can infer the oxygen state of the patient's tissue by knowing the partial pressure of oxygen in the mixed venous blood ($PvO_2$) because of the equilibrium that exists between the partial pressure of oxygen ($PO_2$) in the venous blood and the tissue. As arterial blood passes through the tissues, a partial pressure gradient exists between the $PO_2$ of the blood in the arteriole entering the tissue and the tissue itself. Due to this pressure gradient, oxygen is released from hemoglobin in the red blood cells and also from solution in the plasma; the released 02 then diffuses into the tissue. The $PO_2$ of the blood issuing from the venous end of the capillary cylinder will be a close reflection of the $PO_2$ at the distal (venous) end of the tissue through which the capillary passes.

Under normal conditions the blood $PO_2$ is essentially the same as that of interstitial fluid in contact with the outside of the capillary. The degree of equilibration between blood and tissue may depend on the speed of passage of blood through the capillary bed. If the blood moves through the capillary bed too quickly, the $O_2$ may not have time to diffuse into the tissues. It has also been argued that, under conditions of critical oxygen delivery caused by extreme anemia, there may not be time for equilibration of tissue and the partial pressure of oxygen in the blood. These situations may lead to higher than expected mixed venous $PO_2$ ($PvO_2$). Nevertheless, in the clinical situation, it is generally accepted that the most reliable single physiological indicator for monitoring the overall balance between oxygen supply and demand is mixed venous oxygen tension. As discussed above, one mechanism for determining the mixed venous oxygen tension is through insertion of a pulmonary artery catheter that is passed through the right atrium and the right ventricle of the heart before entering the pulmonary artery by passage through the pulmonary valve.

To fully assess whole body oxygen transport and delivery, one catheter is placed in the patient's pulmonary artery and another in the brachial or femoral artery. Blood samples are then drawn from each catheter to determine the pulmonary artery and arterial blood oxygen levels. The patient's cardiac output may be obtained using the pulmonary arterial catheter by utilizing thermodilution techniques. By injecting a known quantity of a sterile solution at a known temperature into the right atrium of the heart, and then measuring the resultant change in blood temperature at the pulmonary artery, a physician can determine the cardiac output of the patient. Devices such as the Swan-Ganz® thermodilution catheter (Baxter International, Santa Ana, Calif.) are used in such procedures, but they require invasive procedures. While these procedures have proven to be somewhat accurate, they are also quite invasive. Moreover, catheterization can lead to an increased risk of infection, pulmonary artery bleeding from pneumothorax and other complications.

Another method of determining the oxygenation level of a patient's tissue is to measure the level of circulating hemoglobin in the blood. P. Lundsgaard-Hansen, *Infusionstherapie* (1989) 16:167–175. If the hemoglobin level per deciliter of blood in the patient is high, the physician can infer that the patient has sufficient capacity to carry oxygen to the tissue. Unfortunately, measuring the hemoglobin level in a patient only yields a rough estimate of how well the patient's tissues are actually oxygenated. The patient's cardiac output is also an important factor in correlating hemoglobin levels with tissue oxygenation states. Cardiac output is defined as the volume of blood ejected by the left ventricle of the heart into the aorta per unit of time (ml/min) and can be measured with a thermodilution catheter. For example, if a patient has internal bleeding, the concentration of hemoglobin in the blood might be normal, but the total volume of blood will be low. In this situation the heart responds by decreasing the cardiac output to provide better circulation to the tissues. For this reason, simply measuring the amount of hemoglobin in the blood without measuring other parameters such as cardiac output is not always sufficient for estimating the actual oxygenation state of the patient. However, in spite of this a majority of physicians still rely on hemoglobin measurements to gauge whether the patient's oxygenation is stable during surgery because other methods are too invasive.

The Fick equation (Fick, A. Wurzburg, *Physikalisch edizinische Gesellschaft* Sitzungsbericht 16 (1870)) relates the arterial oxygen concentration, venous oxygen concentration and cardiac output to the total oxygen consumption of a patient and can be written as:

$$(CaO_2 - CvO_2) \times CO = VO_2$$

where $CaO_2$ is the arterial oxygen content, $CvO_2$ is the venous oxygen content, $CO$ is the cardiac output and $VO_2$ represents whole body oxygen consumption.

The $VO_2$ level can be calculated from the difference between inspired and mixed expired oxygen and the *minute volume of ventilation.

Others have attempted to non-invasively infer cardiac output by measuring arterial blood pressure instead of relying on thermodilution catheters. For example, Kraiden et al. (U.S. Pat. No. 5,183,051) use a blood pressure monitor to continuously measure arterial blood pressure data. These data are then converted into a pulse contour curve waveform. From this waveform, Kraiden et al. calculate the patient's cardiac output.

During hemodilution, either intentionally as part of an autologous blood conservation program, or following surgical bleeding with maintenance of normovolemia, the Hb concentration and arterial $O_2$ content ($CaO_2$) decrease. As the red cell concentration falls, a reduction in whole blood viscosity occurs. This factor, together with the simultaneous increase in venous blood return, causes a rise in cardiac output (CO). The rise in cardiac output results in improved $O_2$ transport to the tissues ($DO_2$). The degree to which this physiological compensation occurs primarily depends on the CO response to the reduction in red cell mass. Some authorities have concluded that the relationship between a decrease in Hb concentration and increase in CO is linear. (Fan et al, *Am. J. Physiol.* 1980; H545-H552; Robertie and Graylee, *International Anesthesiology Clinics* 1990 28(4):197–204), whereas others have maintained that it follows a curvilinear relationship (Lundsgaard-Hansen, P., *Vox. Sang.* 1979, 36:321–336). However, the degree of curvature found was very minimal, leading many researchers to perform calculations that assume a linear relationship (Hint, H., *Acta Anaesthesiologica Belgica* 1968, 2:119–138).

In man, the extent to which cardiac output rises as Hb concentration decreases can vary between 0.25 liters per minute per gm of Hb change to 0.70 L/min/g. Hence, the cardiac output response to hemodilution differs between patients thereby effecting the Hb level at which additional oxygen carrying capacity in the blood is required. This is one reason that measuring Hb levels is not a good reflection of a patient's tissue oxygenation level. The necessity for red blood cell transfusions also varies depending on such factors as vascular tone, which will cause the viscosity contribution to total systemic resistance to vary, and the ability of the myocardium to function at low Hb levels.

During moderate hemodilution, myocardial blood flow increases proportionately more than total cardiac output and hence, in the absence of significant coronary atherosclerosis, no myocardial ischemia occurs. It has been shown, however, that low postoperative hematocrit (Hct) may be associated with postoperative ischemia in patients with generalized atherosclerosis. Though a number of researchers have attempted to define a critical Hct level most authorities would agree that an empiric automatic transfusion trigger should be avoided and that red cell transfusions should be tailored to the individual patient. The transfusion trigger, therefore, should be activated by the patients own response to anemia—indeed, for patients under anesthesia it is recommended that in the absence of risks, transfusion is not indicated, independent of hemoglobin level.

If $PvO_2$ is accepted as a reasonable indicator of patient safety, the question arises to what can be considered a "safe" level of this parameter. Though much data exists on critical oxygen delivery levels in animals, there is little to indicate what a critical $PvO_2$ might be in the clinical situation. The available data indicates that the level is extremely variable. For instance, in patients about to undergo cardiopulmonary bypass, critical $PvO_2$ varied between about 30 mm Hg and 45 mm Hg (Shibutani et al, *Crit. Care Med.* 1983, 11(8): 640–643); the latter value is well within the range of values found in normal, fit patients. Furthermore, shunting of blood in the tissues will cause elevated levels of $PvO_2$, such as is found in patients in septic shock, and will result in $O_2$ supply dependency (Moshenifar et al, *CHEST* 1983, 84(3): 267–271).

A $PvO_2$ value of 35 mm Hg or more may be considered to indicate that overall tissue oxygen supply is adequate, but this is implicit on the assumption of an intact and functioning vasomotor system. This $PvO_2$ level is reached at a Hb of about 4 g/dL in patients with good cardiopulmonary function. Even lower $PvO_2$ levels are tolerated in some patients when increased fractional inspired $O_2$ concentrations ($FiO_2$s) are employed. During surgery it is necessary to maintain a wide margin of safety and probably best to pick a $PvO_2$ transfusion trigger at which the patient is obviously in good condition as far as oxygen dynamics are concerned. In practice, only certain patients will be monitored with a pulmonary artery catheter; thus, $PvO_2$ will not be available for all patients, leaving the majority to be monitored with the imperfect trigger of Hb concentration. Therefore, a need exists for a system to accurately assess, in real-time, the $PvO_2$ of a patient.

SUMMARY OF THE INVENTION

A system and procedure has been developed to predict, in real-time, a patient's $PvO_2$ under a variety of clinical conditions. This system can replace the imperfect Hematocrit measurement as an indicator of the patient's oxygenation levels. The system uses multiple non-invasive patient inputs to derive a real-time calculation of $PvO_2$.

Overall, the system measures cardiac output derived from an arterial pressure signal taken from the patient. A system such as the Modelflow™ method (TNO-Biomedical Instrumentation, Amsterdam) can be used in the present invention to provide the cardiac output measurement continuously in real-time. A second component of the system of the present invention is a blood chemistry monitor that can continuously measure arterial blood gases and hemoglobin concentrations. From these measurements, the software program of the present invention calculates and displays, in real-time, the $PrO_2$ level of the patient. While the a preferred embodiment of the invention includes a blood chemistry monitor, it is not an essential feature of the invention. For example, a physician could manually measure blood gas levels and hemoglobin concentrations and then enter this information into the Oxyflow system via the keyboard.

The $PvO_2$ level is calculated by using the Fick equation provided above. Specifically, the content of the arterial oxygen ($CaO_2$) is calculated from hemoglobin levels taken from the blood chemistry monitor along with other blood chemistry information such as pH, partial pressure of carbon dioxide ($PCO_2$) and the patient's temperature. The cardiac output (CO) is calculated from arterial pressure using a system such as Modelflow®. The total body oxygenation level ($VO_2$) can be measured by gas analysis, or assumed from the basal metabolic rate of the patient. The Fick equation is then applied, in real-time, and used to derive the content of oxygen in venous blood ($CvO_2$) by using the formula $VO_2=(CaO_2-CvO_2)\times CO$. After the $CvO_2$ has been derived, the $PvO_2$ can be calculated using the Kelman equations (Kelman, *J. Appl. Physiol*, 1966, 21(4): 1375–1376).

One embodiment of the present invention is a method for determining the partial pressure of oxygen in the mixed venous blood ($PvO_2$) of a patient in real-time. This method includes the steps of:

storing constant values corresponding to blood volume, oxygen solubility in plasma and the oxygen content of a desired unit of saturated oxyhemoglobin of a patient into a first computer memory;

measuring the cardiac output values of a patient in real-time, wherein the cardiac output values are saved to a second computer memory;

storing a value corresponding to the whole body oxygen consumption ($VO_2$) of said patient into a third computer memory;

determining the hemoglobin concentration, arterial tension of oxygen ($PaO_2$), arterial tension of carbon dioxide ($CO_2$), arterial pH and body temperature of the patient contemporaneously with the measurement of the cardiac output levels; and calculating the mixed venous blood oxygen tension of a patient in real-time.

Preferably, the first computer memory discussed in the above method is a random access memory (RAM). Similarly, the second computer memory and third computer memory of the above method are advantageously also random access memories. As discussed in the following sections, determining the hemoglobin concentration, arterial tension of oxygen (PaO$_2$), arterial tension of carbon dioxide (CO$_2$), arterial pH and body temperature of the patient preferably utilizes a blood chemistry monitor. In addition, the most preferable method of calculating the mixed venous blood oxygen tension relies on application of the Fick equation.

Another embodiment of the present invention is an apparatus for determining the PvO$_2$ of a patient in real-time. The apparatus includes:

a first computer memory for storing constant values corresponding to blood volume, oxygen solubility in plasma and the oxygen content of a desired unit of saturated oxyhemoglobin;

an input that continuously measures the cardiac output values of a patient in real-time, wherein said cardiac output values are saved in a second computer memory;

first instructions for storing a value corresponding to the whole body oxygen consumption (VO$_2$) of said patient into a third computer memory;

second instructions for obtaining the hemoglobin concentration, arterial tension of oxygen (PaO$_2$), arterial tension of carbon dioxide (CO$_2$), arterial pH and body temperature of said patient contemporaneously with said continuous measurement of the cardiac output levels; and third instructions in said memory for calculating the mixed venous blood oxygen tension of a patient in real-time.

Preferably, the first computer memory, second computer memory and third computer memory are random access memories. In addition, the first computer memory can also advantageously be a computer hard disk. Further, the input used in this apparatus can preferably be an arterial pressure line. In another preferred embodiment, the second instructions can be stored in a blood chemistry monitor. Additionally, the third instructions can preferably utilize an application of the Fick equation. In yet another embodiment of the invention, the second instructions can include instructions for obtaining said patient's hemoglobin concentration, arterial tension of oxygen (PaO$_2$), arterial tension of carbon dioxide (CO$_2$), arterial pH and body temperature from a keyboard input. Alternatively, the second instructions can include instructions for obtaining said patient's hemoglobin concentration, arterial tension of oxygen (PaO$_2$), arterial tension of carbon dioxide (CO$_2$), arterial pH and body temperature from a blood chemistry monitor.

DETAILED DESCRIPTION

The present invention is a system and software program called Oxyflow that can accurately predict the PvO$_2$ of a patient. This system can be used, for example, during surgery to assist the physician in determining the appropriate time to give a blood transfusion. By continuously calculating the patient's PvO$_2$ under a variety of clinical conditions, the system replaces the imperfect Hematocrit measurement as an indicator of tissue oxygenation levels.

The system of the present invention takes multiple inputs from the patient and translates them into a real-time calculation of PvO$_2$. Importantly, the system of the present invention has many advantages over prior measurements of the patient's tissue oxygenation levels. In one important aspect, this system does not require an invasive procedure such as catheterization to determine PvO$_2$. As explained above, invasive procedures such as catheterization can lead to numerous complications for the patient. These complications include increased incidents of infection, bleeding of pneumothorax and other complications related to the procedure. This system has several components which, acting together, provide the entire invention.

I. SYSTEM OVERVIEW

Figure 1:
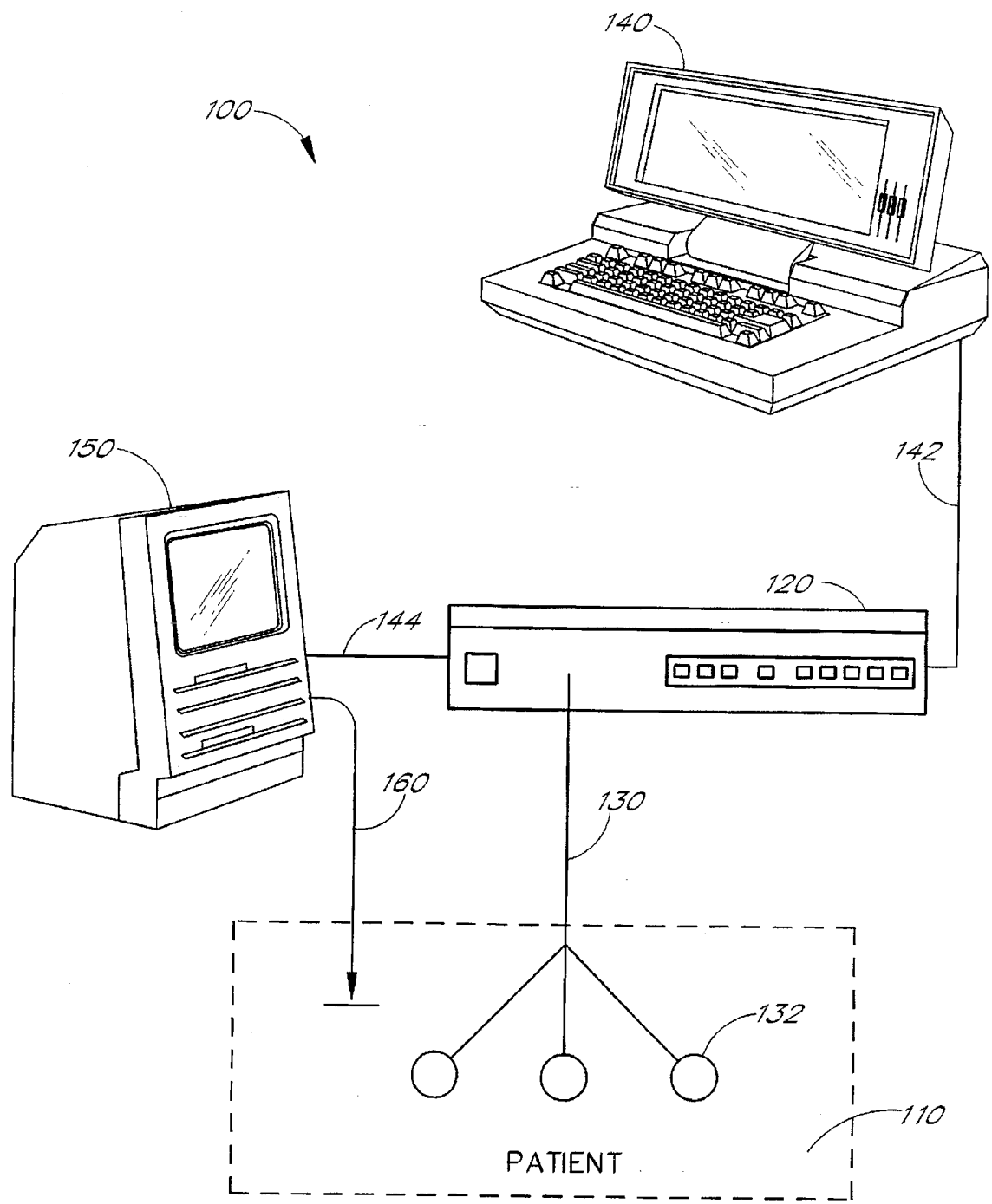
FIG. 1 is diagram of the Oxyflow system including a computer, a converter box, a blood chemistry monitor and a patient.

The Oxyflow system is an online, real-time monitor of cardiac output and mixed venous partial pressure of oxygen. Referring now to FIG. 1, the Oxyflow system 100 provides a physician with real-time data relating to the oxygenation state of a patient. The system works by gathering data from a patient without having to resort to very invasive procedures such as pulmonary artery catheterization.

As shown in FIG. 1, a patient 110 is linked to an interface box 120 via an arterial pressure line and transducer 130 that monitors the patient's arterial pulse wave. The interface box 120 has an RS232 serial port (not shown) which connects to a computer 140 by a serial cable 142. The interface box 120 also contains an analog to digital converter to convert the analog signal from the arterial pressure line 130 into a digital signal. This digital signal is then passed to the computer 140 through the serial line 142. The analog signal from the arterial pressure line 130 is normally sampled at 100 Hz with a resolution of 2.5 mV which is sent over the RS232 serial line and thereafter stored in buffers maintained in the computer's memory. The sampled signals are intermittently saved from the computer memory to the hard disk of the computer.

The data received from the arterial pressure line 130 can be used to calculate, as discussed below, the systolic, diastolic and mean pressure, pulse interval, heart rate and blood ejection time for the heart. In addition, a continuous aortic flow signal can be computed by the computer 140 from a simulated model of the aortic input impedance. Data from the arterial pressure signal can also be used to find the left ventricular stroke volume, which can thereafter be integrated for each heart beat to determine the systemic vascular resistance. These computations are stored in a buffer in the computer's memory and then intermittently saved to the computer's hard disk. As discussed below, the cardiac output is used in the present invention to determine the patient's mixed venous oxygen partial pressure.

A second RS232 serial port on the back of the interface box 120 receives data from the a second serial cable 144 that has been linked to an optional blood chemistry monitor 150. The blood chemistry monitor 150 receives data relaying concentrations of specific components of the patient's arterial blood through an arterial line 160. The blood chemistry monitor 150 measures concentrations of blood components such as pH, hemoglobin levels, arterial oxygen partial pressure and arterial carbon dioxide partial pressures. One of ordinary skill in the art will realize that the information gathered by the blood chemistry monitor can also be manually input into the system. For example, a physician can take blood samples from the patient and manually determine the concentrations of the same blood components as measured by the blood chemistry monitor. The values that are manually determined by the physician can then be entered into the Oxyflow system through the keyboard.

The arterial line 160 repeatedly samples the patient's blood and transmits these blood samples to the sensors of the blood chemistry monitor 150. One preferred blood chemistry monitor is the VIA 1-01 monitor (VIA Medical, San Diego, Calif.). However, other similar types of blood chemistry monitors are anticipated to work in the same manner.

Tying all these hardware components together is the Oxyflow system software. The software controls data gathering from the arterial pressure line 130 and blood chemistry monitor 150. These data are then used to derive the partial pressure of oxygen in the mixed venous blood to provide a real-time, accurate system for a physician.

The Oxyflow software first gathers arterial pressure data from the patient and uses these data to determine the patient's cardiac output. The cardiac output determination can be made using the Modelflo software or another method such as that described in U.S. Pat. No. 5,183,051 to Kraiden.

After the cardiac output has been determined, the arterial pH, hematocrit, $PO_2$ and $PCO_2$ are gathered from the blood chemistry monitor input. Body temperature is either input manually or from a sensor. The blood chemistry monitor continually samples the patient's arterial blood at set time points to identify changes in blood gas/chemistry levels. If a change has taken place in any of the values measured by the blood chemistry monitor, the new value is transmitted to the computer.

In addition to the cardiac output, the total oxygen content ($VO_2$) of the patient can be assumed or determined through standard means. For example, a the Physioflex system from Physio Medical Systems (HAARLEM, Netherlands) can be used to measure the $VO_2$ of a patient.

After the $VO_2$, cardiac output, and arterial oxygen content (from the blood chemistry monitor) are determined, the software of the present invention applies these values to the Fick equation so that the venous oxygen content ($CvO_2$) can be determined. This procedure is explained in more detail below.

Once the $CvO_2$ is known, the mixed venous oxygen content ($PvO_2$) can be derived. Values for mixed venous pH and $PCO_2$ are assumed to have a constant (but alterable) relation in arterial $PCO_2$ and, using the Kelman equations and a "guessed" $PVO_2$, mixed venous content of Hb and Plasma ***$PO_2$ can be calculated. If the $CvO_2$ value will not "fit" the Fick equation, another $PvO_2$ value is chosen. This process is repeated until the Fick equation balances and the true $PvO_2$ is known. The $PvO_2$ value is then continually updated in real-time so that the physician always knows the oxygenation state of the patient. The exact method for performing these functions are described in more detail below.

II. HARDWARE DESCRIPTION

Figure 2:
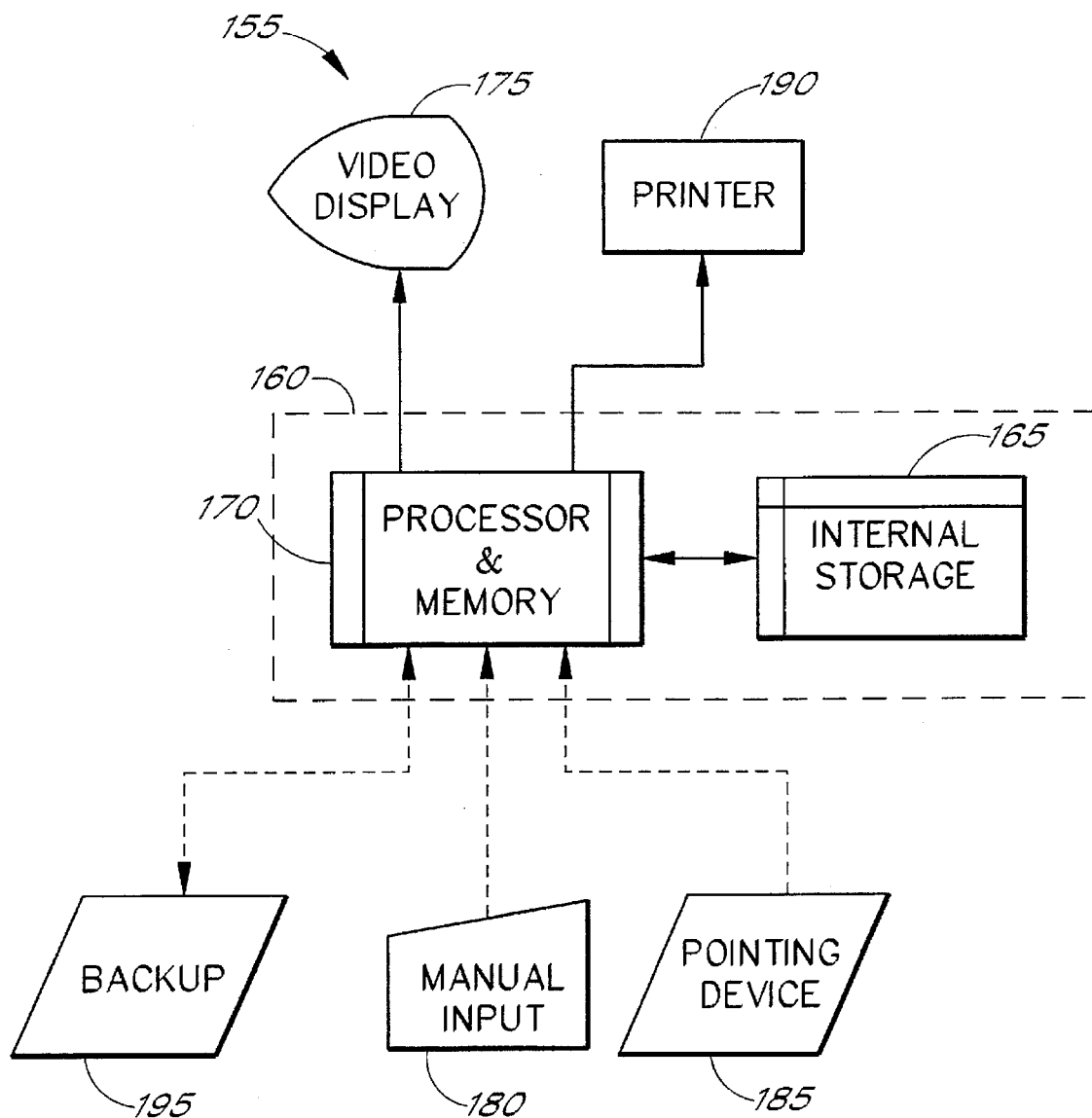
FIG. 2 is a schematic diagram of the computer system that runs the Oxyflow system.

Referring now to FIG. 2, an embodiment of the computer system 155 that controls the peripheral blood monitoring system is shown. The system 155 can be operated in a stand-alone configuration or as part of a network of computer systems. The system 155 is an integrated system which gathers data from the patient and transmits it to the computer.

The desktop system 155 includes the Oxyflow blood monitoring software operating in the MS-DOS, version 6.2 or later, operating system, available from Microsoft Corporation, on computer 160. Although this embodiment is described using the MS-DOS environment on a personal computer, other embodiments may use a different operational environment or a different computer or both.

In an alternate embodiment of the invention, the computer 160 can be connected via a wide area network (WAN) connection to other physicians or hospitals. A WAN connection to other medical institutions enables a real time review of the patient's progress during surgery or in the Intensive Care Unit.

Referring again to FIG. 2, the presently preferred system 155 includes a computer 160, having a minimum of an Intel 80486 or similar microprocessor running at 33 MHz. The computer 160 includes a minimum of four megabytes (MB) of RAM memory (not shown). The system 155 includes a hard disk drive 165 connected to the processor 170. The hard drive 165 is optional in a network configuration, i.e., the workstation uses a hard disk or other storage device in a file server. If computer 160 is used in the stand-alone configuration, the hard drive 165 is preferably 100 Mbytes or more.

The computer 160 is integrated with a group of computer peripherals, and is connected to a VGA (video graphics array) display standard, or better, color video monitor 175, which is required to use all the features of the system 155. A keyboard 180 that is compatible with IBM AT type computers is connected to the computer 160. A pointing device 185, such as a two or three button mouse can also connect to the computer 160. Reference to use of the mouse is not meant to preclude use of another type of pointing device.

The computer 160 connects to a printer 190 to provide a way to produce hard-copy output, such as printouts for file records. In this configuration, a backup device 195, such as a Jumbo 250 Mb cartridge tape back-up unit, available from Colorado Memory Systems, is preferably connected to the computer 160. A hard drive 165 or other similar device is required in the stand-alone configuration.

In an alternate embodiment of a stand-alone configuration, or as one of the workstations of a network configuration, the system 155 may include a portable computer, such as a laptop or notebook computer, e.g., a Premium Executive 386SX/20, available from AST Research, or other computers available from a plurality of vendors. The portable computer (not shown) is equipped with components similar to that described in conjunction with computer 160.

It will be understood by one skilled in the technology that a programmed computer can also be implemented completely or partially with custom circuitry. Therefore, the chosen implementation should not be considered restrictive in any matter.

III. Software Overview

Figure 3:
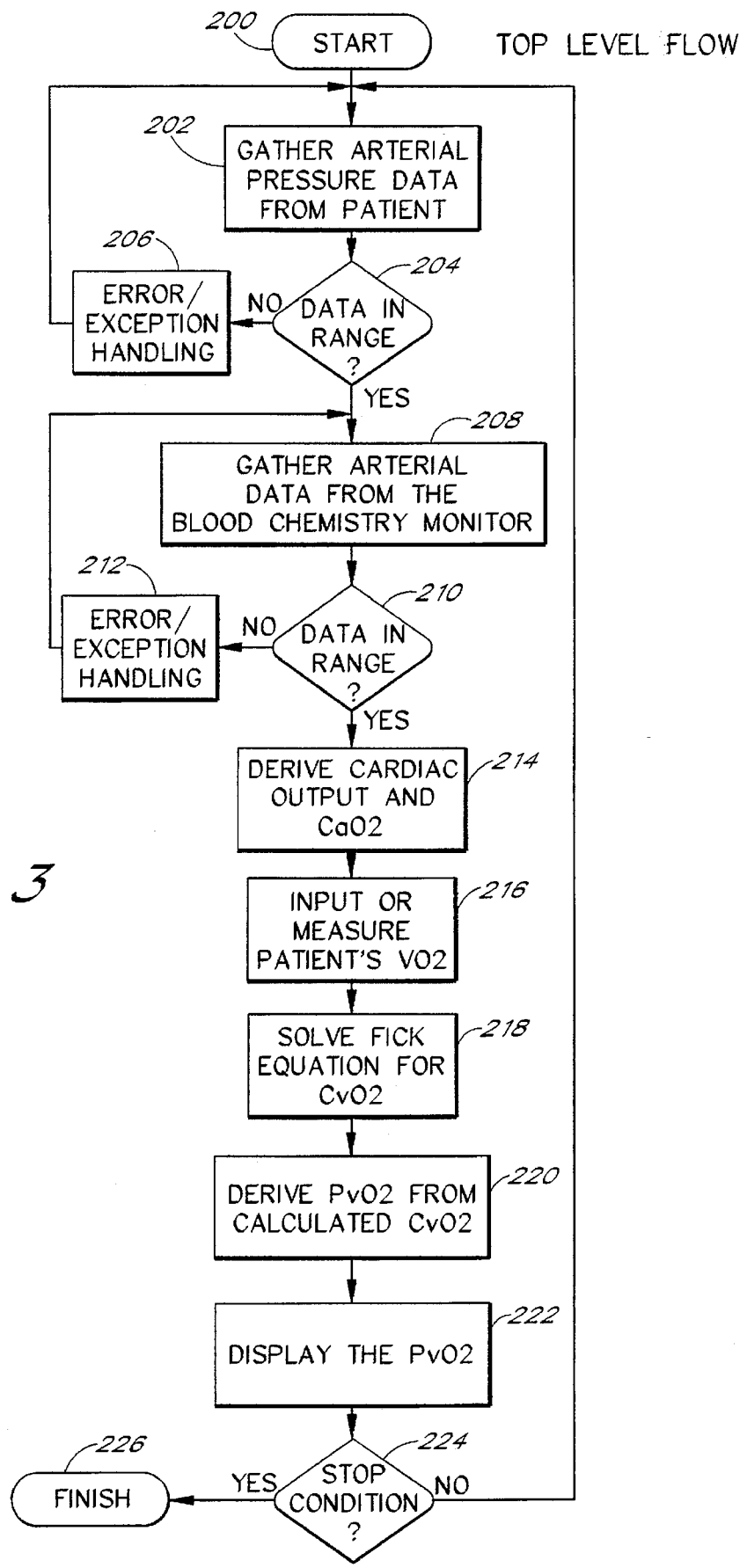
FIG. 3 a flowchart detailing the overall software program that runs the Oxyflow system.

As discussed above, the Oxyflow system of the present invention gathers data from a patient and determines the mixed venous oxygenation state of a patient in real-time. Referring now to FIG. 3, the process is begun when a start signal is transmitted by the user to the system at start state 200. The start signal can be a keystroke of mouse command that initiates the software to begin gathering data. After receiving the start command at state 200, arterial pressure data is gathered from a patient at state 202. Arterial pressure data is gathered by hooking a patient up to an arterial pressure monitor by standard means known to those of skill in the art.

Once data has been gathered from a patient at state 202, a "data in range" decision is made at decision state 204. At this stage, the software compares the data gathered at state 202 with known appropriate ranges for arterial pressure values. Appropriate ranges for arterial pressure data are, for example, between 70/40 and 250/140.

If data gathered at process step 200 is not within the range programmed in decision state 204, an error/exception handling routine is begun at state 206. The error handling routine at state 206 loops the software back to process step 202 to re-gather the arterial pressure data. In this manner, false arterial pressure data readings will not be passed to the rest of the program. If the data gathered at process step 202 is in the appropriate range at decision state 204, the software pointer moves to process step 208 that contains instructions for gathering arterial pH, hemoglobin, $pO_2$ and $pCO_2$ from the attached blood chemistry monitor. This data is gathered by receiving data streams via the serial connection from the blood chemistry monitor into the computer or accessing data that is manually input from the keyboard.

As described previously, the blood chemistry monitor continually samples arterial blood from the patient. The blood chemistry monitor determines several properties of the patient's blood from each sample. Data corresponding to each of the properties taken from the blood chemistry monitor at process step 208 are also checked so that they are in range at decision state 210. Appropriate ranges for the pH are 7.15 to 7.65. Art appropriate range for the hemoglobin level is from 0 to 16. An appropriate range for the $PaO_2$ is from 50 to 650. Similarly, an appropriate range for the $PCO_2$ is from 15 to 75.

If data is not in the appropriate range for each specific variable at decision state 210, an error/exception handling routine at state 212 is begun. The error/exception handling routine at state 212 independently analyses each variable gathered at state 208 to determine whether it is in range. If one of the variables gathered at state 208 is not within the appropriate range, the error/exception handling routine 212 loops a software pointer back to state 208 so that accurate data can be gathered. If the data is in range at decision box 210, then the software derives the cardiac output from the arterial pressure at state 214.

As discussed previously, cardiac output can be derived from arterial pressure measurements by any number of methods. For example, the Modelflow® system from TNO Biomedical can derive a cardiac output value in real-time from an arterial pressure signal. Other methods, as discussed above, could also be used at process step 214 to determine cardiac output. Once a cardiac output value has been determined at process step 214, the $VO_2$ of the patient is measured or input at state 216.

The patient's $VO_2$ can be measured by hooking the patient up to a suitable ventilator and measuring his oxygen uptake through a system such as the Physioflex discussed above. By determining the amount of oxygen inspired and expired, the physician can calculate and input into the program the total amount of oxygen absorbed by the patient. After the patient's $VO_2$ value has been determined based on a basal metabolic rate at process step 216, these variables are applied to the Fick equation at state 218. The Fick equation is provided above.

Once the $CvO_2$ is known, the mixed venous oxygen content ($PvO_2$) can be derived at state 220. Values for mixed venous pH and $PCO_2$ are assumed to have a constant (but alterable) relation in arterial $PCO_2$ and, using the Kelman equations and a "guessed" $PvO_2$, mixed venous content of Hb and Plasma ***$PO_2$ can be calculated. If the $CvO_2$ value will not "fit" the Fick equation, another $PvO_2$ value is chosen. This process is repeated until the Fick equation balances and the true $PvO_2$ is known.

After deriving the mixed venous oxygen pressure of the patient's blood, it is displayed on the computer screen at step 222. If the software has not received a keyboard or mouse input to stop gathering data at decision state 224, a pointer loops the program back to process state 202 to begin gathering arterial pressure data again. In this manner, a real-time data loop continues so that the patient's mixed venous partial pressure of oxygen is constantly updated and displayed on the computer at state 222. If the software has received a stop command from a keyboard or mouse input at decision state 224, then a finish routine 226 is begun.

Software Implementation

Many different ways of implementing the software of the present invention will be known to those with ordinary skill in the art. For example, programming languages such as C++, Basic, Cobol, Fortran or Modula-2 can be used to integrate the features of the present invention into one software package. An alternative method of producing the software of the present invention is to use a spreadsheet program to gather and determine the $PvO_2$ of a patient in real-time. This method is described in detail below.

The following system utilizes a large Microsoft Excel® spreadsheet to gather information from the patient and derive the $PvO_2$. Before receiving real-time inputs of cardiovascular and oxygenation variables, a number of constants are entered into the system. These constants include the patient's blood volume, oxygen solubility in plasma and the oxygen content of 1 g of saturated oxyhemoglobin. These constants are then stored in the computer's memory for use in later calculations.

TABLE 1 shows commands from part of a Microsoft Excel® spreadsheet that gathers a patient's data and derives, the value of $PvO_2$. The program is initialized by assigning names to various constants that are to be used throughout the software. Constants corresponding to Blood Volume (BV), Oxygen solubility in a perfluorocarbon emulsion (O2SOL), Specific Gravity of any perfluorocarbon emulsion (SGPFOB), intravascular half-life of a perfluorcarbon emulsion (HL), weight/volume of a perfluorcarbon emulsion (CONC), barometric pressure at sea level (BARO), milliliters oxygen per gram of saturated hemoglobin (HbO) and milliliters of oxygen per 100 ml plasma per 100 mm of mercury (PIO) are all input into the software.

An example of the starting values for these constants is shown in TABLE 1. These starting values are used in later calculations to derive the patient's mixed venous oxygenation state. The software program of the present invention also uses Kelman constants in calculating the $PvO_2$ of a patient. The Kelman constants are also assigned names as shown in TABLE 1.

TABLE 1

| ASSUMPTIONS: | VALUES AT START: |
|---|---|
| Blood Volume (ml/kg) -BV | 70 |
| $O_2$ solubility in PFB (ml/dl @ 37 deg C.) -O2SOL | 52.7 |
| Specific Gravity of PFOB -SGPFOB | 1.92 |
| Intravascular half-life of Oxygent HT hours -HL | =½ Life of $O_2$ |
| Wgt/Vol of PFOB emulsion/100 -CONC | 0.6 |
| Barometric Pressure @ sea level -BARO | 760 |
| Ml O2 per gram saturated Hb -HbO | 1.34 |
| Ml O2 per 100 ml plasma per 100 mm Hg -HIO | 0.3 |
| KELMAN CONSTANTS: | VALUES AT START |
| Ka1 | =−.8.5322289*1000 |
| Ka2 | = 2.121401*1000 |
| Ka3 | =−.6.7073989*10 |
| Ka4 | = 9.3596087*100000 |
| Ka5 | =−3.1346258*10000 |
| Ka6 | =2.3961674*1000 |
| Ka7 | −67.104406 |
| Total dose of Oxygent in g/kg PFC | =weight per volume PFB * Intravascular Oxygent HT Dose (ml/kg) |
| ½ life of PFC (Hrs) | =−0.038819 + (1.6043 * Total Oxygent Dose) + (0.248 * Total Oxygent Dose^2) |

After these constants have been assigned names, the real time inputs from the arterial pressure lines and blood chemistry monitor are initialized to begin receiving data. As shown in TABLE 2, the system receives data for the arterial oxygen saturation percentage ($SaO_2$), mixed venous oxygen saturation percentage ($SvO_2$), derived from arterial oxygen partial pressure ($PaO_2$), arterial pH (pHa), arterial pressure of carbon dioxide ($PaCO_2$) and body temperature (TEMP), calculated mixed venous oxygen partial pressure ($PvO_2$) makes the mixed venous pH (pHv), mixed venous partial pressure of carbon dioxide ($PvCO_2$). Cardiac output (CO) is also input as in $VO_2$.

When Hb concentration, arterial and mixed venous blood gas and acid/base parameters are entered into the program, the $O_2$ delivery and consumption variables for both red cell containing Hb and for the plasma phase will be determined. These vesicles relating to PFC or Hb based oxygen carrier can also be determined.

Input variables concerned with calculation of $CaO_2$ include Hb concentration, arterial tension of oxygen ($PaO_2$) and carbon dioxide ($PaCO_2$), arterial pH (pHa) and body temperature. The position of the oxyhemoglobin dissociation curve is calculated using the Kelman equations which are input as constants in the program. These calculations produce a curve that, over the physiological range of $O_2$ tensions, is indistinguishable from the parent curve proposed by Severinghaus (*J. Appl. Physiol.* 1966, 21: 1108–1116).

The primary and most important output of the program is $PvO_2$, which can help the physician determine when to give the patient a blood transfusion or in other ways alter the patient's clinical management. The amount of blood that must be removed in order to hemodilute a patient to a certain Hb concentration can be calculated and the amount of Hb present in individual blood "units" removed during the hemodilution procedure are also available.

TABLE 2

| INPUTS: | AT START: |
|---|---|
| Hemoglobin (Gm/dl) -Hb | 6 |
| Desired End Hemodilution Hb -HbEND | 15 |
| Arterial Oxygen Saturation (%) -SaO2 | |
| Calculated Arterial Oxygen Saturation (%) -SaO2CALC | =100*(SPaO2*(SPaO2*(SPaO2 (SPaO2 + Ka3) + Ka2) + Ka1))/(SPaO2*(SPaO2*(SPaO2*(SPaO2 + Ka7) + Ka6) + Ka5) + K |
| Active Input Value for SaO2 -SaO2USED | =IF(SaO2<>0,SaO2,SaO2CALC) |
| Mixed Venous Oxygen Saturation (%) -SvO2 | |
| Calculated Mixed Venous Oxygen saturation -SVO2CALC | =100*(SPvO2*(SPvO2*(SPvO2 (SPvO2 + Ka3) + Ka2) + Ka1))/SPvO2*(SPvO2*(SPvO2*(SPvO2 + Ka7) + Ka6) + Ka5) + K |
| Active Input Value for SvO2 -SvO2USED | =IF(SvO2<>0,SvO2,SvO2CALC) |
| Arterial Oxygen Partial Pressure (mm Hg) -PaO2 | 100 |
| Calculated 'standardized' PaO2 -SPaO2 | =PaO2*10^((0.024*(37-TEMPUSED)) + (0.4*(pHaUSED-7.4)) + (0.06*(LOG10(40)-LOG10(PaCO2USED)))) |
| Active Input Value for PaSO2 -PaSO2USED | =IF(PaO2<>0,PaO2,SPaO2) |
| Arterial pH - pHa | |
| Normal Arterial pH -pHaNORM | 7.4 |
| Active Input Arterial pH -pHaUSED | =IF(pHa<>0,pHa,pHaNORM) |
| Arterial PCO2 -PaCO2 | |
| Normal PaCO2 -PaCO2NORM | 40 |
| Active Input Arterial PCO2 -PaCO2USED | =IF(PaCO2<>0,PaCO2,PaCO2NORM) |

TABLE 2-continued

| INPUTS: | AT START: |
|---|---|
| Body Temp C. -TEMP | |
| Normal Body Temp C. -TEMPNORM | 37 |
| Active Input Body Temp C. -TEMPUSED | =IF(TEMP<>0,TEMP,TEMPNORM) |
| Mixed Venous Oxygen Partial Pressure (mm Hf) -PvO2 | 40.6819722973629 |
| Calculated 'standardized' PvO2 -SPvO2 | =PvO2*10^((0.024*(37-TEMPUSED)) + (0.4*(pHvUSED-7.4)) + (0.06*(LOG10(40)-LOG10(PvCQ2USED)))) |
| Mixed Venous pH -pHv | |
| Normal Venous pH | 7.4 |
| Active Input Mixed Venous pH -pHvUSED | =IF(pHv<>0,pHv,pHvNORM) |
| Mixed Venous PCO2 -PvCO2 | |
| Normal Mixed Venous PCO2 - PvCO2NORM | 40 |
| Active Input Mixed Venous PCO2 -PvCO2USED | =IF(PvCO2<>0,PvCO2,PvCO2NORM) |
| Cardiac Output (l/mm) -CO | =((14 - Hemoglobin (gm/dl) * CO Response to 1 gram of Hb Depletion) + 5 |
| Co Response to 1 gr Hb depletion -COCHG | 0.7 |
| Intravascular Oxygen HT Dose(ml/kg) -PFB | |
| Time Adj. Intravascular Oxygen HT Conc(ml/kg) -TAPFB | |
| Patient's Weight (kg) -kg | 70 |
| Total O2 Consumption (ml/min/kg) -VO2KG | 3 |
| Calculated Blood Volume (ml) -CBV | =BV*kg |
| Calc input Total O2 Consumption (ml/min/kg) -VO2 | =kg*VO2KG |
| Bleeding Rate (liters/hour) -BR | 1 |
| Exchange Volume (ml) -EV | 100 |

TABLE 3

| DESCRIPTION: | CALCULATIONS: |
|---|---|
| Arterial O2 Content in Hemoglobin (ml/dl) -CaO2Hb | =((Hb*HbO*SaO2USED)/100) |
| Arterial O2 Content in Plasma (ml/dl) -CaO2Pl | =((PaO2*PIO)/100) |
| Arterial O2 Content in PFB (ml/dl)) -CaO2PFB | =((PFB*kg*CONC)/SGPFOB)/ (kg*BV*0.01)*((O2SOL*PaO2)/(100*BARO)) |
| Arterial Oxygen Content (ml/dl) -CaO2 | =(CaO2Hb + CaO2Pl + CaO2PGB) |
| Mixed Venous O2 Content in Hemoglobin (ml/dl)) -CvO2Hb | =((Hb*HbO*SvO2USED)/100) |
| Mixed Venous O2 Content in Plasma (ml/dl) -CvO2Pl | =((PvO2*PIO)/100) |
| Mixed Venous O2 Content in PFB (ml/dl) -CvO2PFB | =((PFB*kg*CONC)/SGPFOB)/ (kg*BV*0.01)*((O2SOL*PvO2)/(100*BARO)) |
| Mixed Venous Oxygen Content (ml/dl) -CvO2SUM | =(CvO2Hb + CvO2Pl + CvO2PFB) |
| Mixed Venous Oxygen Content (ml/dl) -CvO2 | =IF(CVO2SUM>0,(CVO2SUM),CvO2CALC2) |
| Mixed Venous O2 Content (ml/dl) -CvO2CALC2 | =CaO2-(VO2/(CO*10)) |
| Total Blood loss (ml) - TBL | |
| Autologous Hb Available (grams)-AHbA | |
| Autologous Hb Available (grams) in 1st unit-AHbA1 | =C105 |
| Autologous Hb Available (grams) in 2nd unit-AHbA2 | =IF(OFFSET(Hb,0,8)<=OFFSET(HbEND,0,8),**,C106-C105) |
| Autologous Hb Available (grams) in 3rd unit-AHbA3 | =IF(OFFSET(Hb,0,12)<=OFFSET(HbEND,0,12),**,C107,B106,B105) |
| Autologous Hb Available (grams) in 4th unit-AHbA4 | =IF(OFFSET(Hb,0,16)<=OFFSET(HbEND,0,16),**,C108,B107,B106,B105) |
| Autologous Hb Available (grams) in 5th unit-AHbA5 | =IF(OFFSET(Hb,0,20)<= OFFSET(HbEND,0,20),**,C109,B108,B107,B106,B105) |
| Autologous Hb Available (grams) in 6th unit-AHbA6 | =IF(OFFSET(Hb,0,24)<= OFFSET(HbEND,0,24),**,C110,B109,B108,B107,B106,B105) |
| Autologous Hb Available (grams) in 7th unit-AHbA7 | =IF(OFFSET(Hb,0,28)<= OFFSET(HbEND,0,28),**,C111,B110,B109,B108,B107,B106,B105) |
| Autologous Hb Available (grams) in 8th unit-AHbA8 | =IF(OFFSET(Hb,0,32)<= OFFSET(HbEND,0,32),**,C112,B111,B110,B109,B108,B107,B106,B105) |
| Autologous Hb Available (grams) in 9th unit-AHbA9 | =IF(OFFSET(Hb,0,36)<= OFFSET(HbEND,0,36),**,C113,B112,B111,B110,B109,B108,B107,B106,B105) |
| Autologous Hb Available (grams) in 10th unit-AHbA10 | =IF(OFFSET(Hb,0,40)<= OFFSET(HbEND,0,40),**, C114,B113,B112,B111,B110,B109,B108,B107,B106,B105) |
| Percent of VO2 provided from plasma | =($O_2$ Used From Plasma/Active Input Total $O_2$ Consumption) * 100 |
| Percent VO2 provided by PFB | =100 * ($O_2$ Used From Perflubron/Active Input Total $O_2$ Consumption) |
| Percent of VO2 provided by plasma and PFB | =100 * (($O_2$ Used From Plasma + $O_2$ Used From Perflubron/Active Input Total $O_2$ Consumption) * 100 |

TABLE 4

| DESCRIPTION: | OUTPUTS: |
| --- | --- |
| Total Oxygen Transport (ml/min) -TDO2 | =CaO2*CO*10 |
| O2 Transport in Hemoglobin (ml/min) - DO2Hb | =(CaO2Hb)*CO*10 |
| O2 Transport in plasma (ml/min) -DO2PI | =CaO2PI*CO*10 |
| O2 Transport in Perflubron (ml/min) -DO2PFB | =CaO2PFB*CO*10 |
| Calc Total O2 Consumption (ml/min) -VO2CALC | =(CaO2-CvO2)*CO*10 |
| Active Input Total O2 Consumption (ml/min) -VO2USED | =IF(VO2<>0,VO2,VO2CALC) |
| Oxygen Used from Hemoglobin (ml/min) -VO2Hb | =(CaO2Hb-CvO2Hb)*CO*10 |
| Oxygen Used from Plasma (ml/min) -VO2PI | =(CaO2PI-CvO2PI)*(CO*10) |
| Oxygen used from Perflubron (ml/min) -VO2PFB | =(CaO2PFB-CvO2PFB)*(CO*10) |
| Total Oxygen Extraction Coefficient -OEC | =(CaO2-CvO2)/CaO2 |
| Hemoglobin Oxygen Extraction Coefficient -HOEC | =(SaO2USED-SvO2USED)/SaO2USED |

As explained, the present system allows a physician to determine the tissue oxygenation state of a patient, in real time, during surgery. The above-described method uses a Microsoft Excel® spreadsheet. However, one of ordinary skill in the art could integrate the above-referenced spreadsheet with the Modelflo system and still be within the purview of the present invention. For example, software instructions written in other languages such as C++, Cobol, Fortran and basic could also carry out similar functions to the Excel® spreadsheet disclosed herein. The present invention is not limited to the embodiment of the Oxyflow system disclosed herein, but should only be limited by the following claims.

We claim:

1. A method for determining mixed venous blood oxygen tension ($PvO_2$) of a patient in real-time, comprising the steps of:

storing constant values corresponding to blood volume, oxygen solubility in plasma and oxygen content of a desired unit of saturated oxyhemoglobin of a patient into a first computer memory;

measuring cardiac output values (CO) of a patient in real-time, wherein said cardiac output values are saved to a second computer memory;

storing a value corresponding to whole body oxygen consumption ($VO_2$) of said patient into a third computer memory;

determining arterial oxygen content ($CaO_2$) of said patient using numerical values corresponding to hemoglobin concentration, arterial tension of oxygen ($PaO_2$), arterial tension of carbon dioxide ($CO_2$), arterial pH and body temperature wherein said values are obtained contemporaneously with said measurement of cardiac output levels; and calculating the mixed venous blood oxygen tension ($PvO_2$) of a patient in real-time.

2. The method of claim 1 further comprising the step of accessing a random access memory for use as said first computer memory.

3. The method of claim 1 further comprising the step of accessing a random access memory for use as said second computer memory.

4. The method of claim 1 further comprising the step of accessing a random access memory for use as said third computer memory.

5. The method of claim 1 further comprising the step of utilizing a blood chemistry monitor to determine one or more numerical values corresponding to hemoglobin concentration, arterial tension of oxygen ($PaO_2$), arterial tension of carbon dioxide ($CO_2$), arterial pH and body temperature.

6. The method of claim 1 further comprising the step of employing an equation having the formula $$(CaO_2-CvO_2) \times CO = VO_2$$

wherein $CaO_2$ is arterial oxygen content, $CvO_2$ is venous oxygen content, CO is cardiac output and $VO_2$ represents whole body oxygen consumption, to calculate the mixed venous blood oxygen tension of said patient.

7. An apparatus for determining mixed venous blood oxygen tension ($PvO_2$) of a patient in real-time, comprising:

a first computer memory for storing constant values corresponding to blood volume, oxygen solubility in plasma and oxygen content of a desired unit of saturated oxyhemoglobin;

an input that measures cardiac output values (CO) of a patient in real-time, wherein said cardiac output values are saved in a second computer memory;

first instructions for storing a value corresponding to whole body oxygen consumption ($VO_2$) of said patient into a third computer memory;

second instructions for obtaining arterial oxygen content ($CaO_2$) of said patient using values corresponding to hemoglobin concentration, arterial tension of oxygen ($PaO_2$), arterial tension of carbon dioxide ($CO_2$), arterial pH and body temperature wherein said values are obtained contemporaneously with said continuous measurement of the cardiac output levels; and third instructions in said memory for calculating the mixed venous blood oxygen tension ($PvO_2$) of a patient in real-time.

8. The apparatus of claim 7 wherein said first computer memory is a random access memory.

9. The apparatus of claim 7 wherein said second computer memory is a random access memory.

10. The apparatus of claim 7 wherein said third computer memory is a random access memory.

11. The apparatus of claim 7 wherein said computer memory is a hard disk.

12. The apparatus of claim 7 wherein said input is an arterial pressure line.

13. The apparatus of claim 7 wherein said second instructions are stored in a blood chemistry monitor.

14. The apparatus of claim 7 wherein said third instructions utilize an equation having the formula $$(CaO_2-CvO_2) \times CO = VO_2$$

wherein $CaO_2$ is arterial oxygen content, $CvO_2$ is venous oxygen content, CO is cardiac output and $VO_2$ represents whole body oxygen consumption.

15. The apparatus of claim 7 wherein said second instructions include instructions for obtaining said patient's hemoglobin concentration, arterial tension of oxygen ($PaO_2$), arterial tension of carbon dioxide ($CO_2$), arterial pH and body temperature from a keyboard input.

16. The apparatus of claim 7 wherein said second instructions include instructions for obtaining said patient's hemoglobin concentration, arterial tension of oxygen ($PaO_2$), arterial tension of carbon dioxide ($CO_2$), arterial pH and body temperature from a blood chemistry monitor.

* * * * *